United States Patent [19]

Green et al.

[11] Patent Number: 5,489,287
[45] Date of Patent: Feb. 6, 1996

[54] APPARATUS AND METHOD FOR SUBCUTICULAR STAPLING OF BODY TISSUE

[75] Inventors: David T. Green, Westport; Henry Bolanos, East Norwalk, both of Conn.

[73] Assignee: United States Surgical Corporation, Norwalk, Conn.

[21] Appl. No.: 195,902

[22] Filed: Feb. 10, 1994

Related U.S. Application Data

[63] Continuation of Ser. No. 630,224, Dec. 19, 1990, abandoned, which is a continuation-in-part of Ser. No. 581,776, Sep. 13, 1990, abandoned.

[51] Int. Cl.⁶ .................................................. A61B 17/04
[52] U.S. Cl. ........................ 606/139; 606/219; 227/176.1; 411/451; 411/487; 411/488; 411/498
[58] Field of Search ................................ 606/142, 144, 606/139, 215, 216, 219, 220, 187–188; 227/176, 177; 411/451, 455, 487, 489, 498

[56] References Cited

U.S. PATENT DOCUMENTS

| 2,182 | 7/1841 | Ballard | 411/452 |
|---|---|---|---|
| 415,175 | 11/1889 | Prouty | 206/344 |
| 715,612 | 12/1902 | Van Schott . | |
| 816,026 | 3/1906 | Meier . | |
| 1,200,594 | 10/1916 | Curtis . | |
| 1,452,373 | 4/1923 | Gomez . | |
| 1,906,527 | 5/1933 | Bradley | 411/451 |
| 1,933,317 | 10/1933 | Curtis . | |
| 2,254,620 | 9/1941 | Miller . | |
| 2,356,376 | 8/1944 | Brown, Jr. | 411/451 |
| 2,668,538 | 2/1954 | Baker . | |
| 2,811,971 | 11/1957 | Scott . | |
| 2,910,067 | 10/1959 | White . | |
| 3,110,899 | 11/1963 | Warren | 606/139 |
| 3,150,379 | 9/1964 | Brown . | |
| 3,203,220 | 8/1965 | Kaepernik . | |
| 3,205,757 | 9/1965 | Kuennen . | |
| 3,378,010 | 4/1968 | Codling et al. . | |

(List continued on next page.)

FOREIGN PATENT DOCUMENTS

| 256506 | 5/1963 | Australia . | |
|---|---|---|---|
| 017345 | 3/1986 | European Pat. Off. . | |
| 0392750 | 10/1990 | European Pat. Off. | 227/19 |
| 2308349 | 11/1976 | France | 606/216 |
| 2740274 | 3/1978 | Germany | 606/216 |
| 8522122 | 10/1985 | Germany . | |
| 166352 | 3/1984 | Switzerland . | |
| 888965 | 12/1981 | U.S.S.R. | 606/144 |
| 1210801 | 2/1986 | U.S.S.R. . | |
| 873960 | 8/1959 | United Kingdom | 411/455 |
| 1350100 | 4/1974 | United Kingdom | 606/138 |
| 2162782 | 2/1986 | United Kingdom . | |
| 1172775 | 12/1986 | United Kingdom | 227/175 |
| 8503857 | 9/1985 | WIPO | 606/72 |
| 8901767 | 3/1989 | WIPO . | |

OTHER PUBLICATIONS

"United States Surigical Corporation Information Booklet for Auto Suture® Purse String Instrument", copyright 1977, 1978, United States Surgical Corporation.
Peacock, Erle E., *Wound Repair*, 1984, 141–158.

*Primary Examiner*—Gary Jackson

[57] ABSTRACT

A surgical apparatus is disclosed for attaching adjacent end portions of cutaneous body tissue wherein a pair of opposed jaws have means for moving the jaws toward and away from each other. Body tissue engaging means in the form of sharp tip members extend from each jaw and toward the other so as to engage the opposed portions of cutaneous tissue when the jaws are positioned thereagainst and moved toward each other. The jaws and the tips are arranged to cause the cutaneous tissue to assume an irregular shape at the interface whereby an elongated rod-like member, preferably rectangular in cross section, may be directed generally medially of the interface of the tissue to attach the opposed portions to thereby permit healing. The elongated member may have indentations to improve retention within the tissue. A tapered distal end of the elongated member has a pointed tip to facilitate penetration into the tissue.

19 Claims, 4 Drawing Sheets

U.S. PATENT DOCUMENTS

| | | | |
|---|---|---|---|
| 3,618,447 | 11/1971 | Goins | 411/451 |
| 3,631,707 | 1/1972 | Miller . | |
| 3,716,058 | 2/1973 | Taner, Jr. . | |
| 4,052,988 | 10/1977 | Doddi et al. . | |
| 4,064,881 | 12/1977 | Meredith . | |
| 4,162,678 | 7/1979 | Fedotov et al. | 227/19 |
| 4,164,225 | 8/1979 | Johnson et al. . | |
| 4,256,251 | 3/1981 | Moshofsky | 227/120 |
| 4,345,600 | 8/1982 | Rothfuss . | |
| 4,399,810 | 8/1983 | Samuels et al. | 606/19 |
| 4,448,194 | 5/1984 | DiGiovanni et al. | 227/67 |
| 4,493,322 | 1/1985 | Becht | 227/177 |
| 4,506,669 | 3/1985 | Blake, III . | |
| 4,523,591 | 6/1985 | Kaplan et al. . | |
| 4,523,695 | 6/1985 | Braun et al. | 227/19 |
| 4,526,173 | 7/1985 | Sheehan | 606/216 |
| 4,527,725 | 7/1985 | Foslien | 227/19 |
| 4,535,772 | 8/1985 | Sheehan . | |
| 4,595,007 | 6/1986 | Mericle . | |
| 4,605,002 | 8/1986 | Rebuffat . | |
| 4,610,251 | 9/1986 | Kumar . | |
| 4,612,923 | 9/1986 | Kronenthal . | |
| 4,688,560 | 8/1987 | Schulz . | |
| 4,712,550 | 12/1987 | Sinnett | 411/455 |
| 4,744,365 | 5/1988 | Kaplan et al. . | |
| 4,753,636 | 6/1988 | Free | 604/49 |
| 4,815,468 | 3/1989 | Annand | 606/216 |
| 4,832,026 | 5/1989 | Jones . | |
| 4,834,098 | 5/1989 | Jones . | |
| 4,841,960 | 6/1989 | Garner | 606/216 |
| 4,858,603 | 8/1989 | Clemow et al. . | |
| 4,865,032 | 9/1989 | Jones | 606/216 |
| 4,869,242 | 9/1989 | Galluzzo . | |
| 4,873,976 | 10/1989 | Schrieber . | |
| 4,874,122 | 10/1989 | Froehlich et al. . | |
| 4,887,756 | 12/1989 | Puchy | 227/19 |
| 4,895,148 | 1/1990 | Bays et al. . | |
| 4,898,186 | 2/1990 | Ikada et al. | 606/62 |
| 4,899,745 | 2/1990 | Laboureau et al. | 606/142 |
| 4,924,866 | 5/1990 | Yoon | 606/216 |
| 4,944,742 | 7/1990 | Clemow et al. . | |
| 4,973,211 | 11/1990 | Potucek | 411/452 |
| 4,976,686 | 12/1990 | Ball et al. | 604/61 |
| 5,004,469 | 4/1991 | Palmieri et al. | 606/139 |
| 5,007,921 | 4/1991 | Brown . | |
| 5,026,374 | 6/1991 | Dezza et al. . | |
| 5,047,047 | 9/1991 | Yoon | 606/216 |
| 5,156,609 | 10/1992 | Nakao et al. | 606/142 |
| 5,158,566 | 10/1992 | Pianetti | 606/216 |

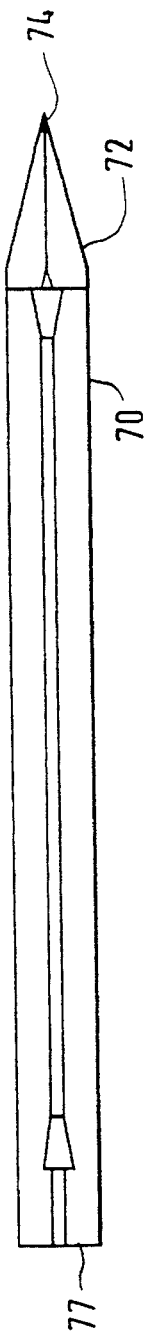
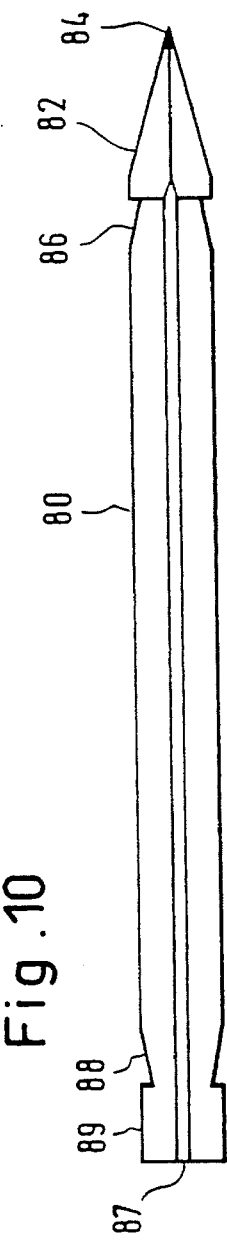
Fig. 9   Fig. 10   Fig. 11   Fig. 12

APPARATUS AND METHOD FOR SUBCUTICULAR STAPLING OF BODY TISSUE

BACKGROUND OF THE INVENTION

This is a continuation of application No. 07/630,224, filed on Dec. 19, 1990, now abandoned, which is a continuation-in-part of application No. 07/581,776, filed on Sep. 13, 1990, now abandoned.

1. Field of the Invention

The present invention relates to an apparatus and method for subcuticular attachment of skin surrounding an opening wherein the opening is either caused unintentionally or by surgical procedure.

2. Description of the Prior Art

Modern day surgery using sutures and staples or the like is well defined. Generally, the key to successfully attaching cutaneous matter is the utmost gentleness in handling all tissue. Damaged and injured tissue leads to necrosis followed by fibrosis and scarring.

In handling tissue for attaching the surgical ends adjacent an opening, care must be taken in attaching the open ends to provide a minimum of the usual well-known telltale marks in the skin. For example, the application of sutures in cutaneous surgery will often result in the appearance of telltale crosshatch markings, whereas the use of sutures subcutaneously allows for early removal to minimize the telltale marks. Application of subcutaneous sutures generally refers to introduction of sutures at well below the epidermis and dermis. Subcuticular sutures generally refer to sutures introduced beneath the epidermis. In any event, reference to attachment of cutaneous matter below the epidermis at any level is sometimes referred to as "subcutaneous".

Surgically attaching cutaneous matter is also accomplished by application of staples which are generally of a metal material and are closed by action against an anvil which causes the ends of the staple to close after piercing the skin surrounding an opening. In either case, the portions of skin are first drawn together and then stapled or sutured so as to hold them together until natural healing takes place. The steps are often cumbersome to the surgeon since holding the skin together requires one motion and stapling or suturing requires another.

To date, there does not appear to exist an apparatus which is capable of gripping the portions of cutaneous matter surrounding an opening and drawing them together, followed by introduction of a staple at subcuticular levels, i.e. below the epidermis. Neither does there appear to exist an apparatus which is capable of drawing the cutaneous matter together and firing a staple in the subcutaneous region, i.e. in the region below the dermis. The present invention is directed to such an apparatus and method for attachment of cutaneous matter.

SUMMARY OF THE INVENTION

A surgical apparatus for attaching at least two adjacent end portions of a medium such as cutaneous body tissue which comprises a pair of jaws, means for moving the jaws toward and away from each other, and body tissue engaging means extending from each jaw and facing the opposed jaw and adapted to engage the respective opposed portions of the medium such that when the jaws are moved toward each other said engaging means causes the two end portions of the medium to be displaced toward each other and to assume an irregular or undulating shape whereby an elongated member may be directed generally medially of the medium to thereby attach opposed portions of the medium.

Means is provided to direct an elongated attaching member generally medially of the interface and subcuticularly of the body tissue to thereby attach the end portions. Preferably, each jaw includes a sharp pointed member positioned for engagement with marginal end portions of skin adjacent an opening therein such that when the jaws are displaced toward each other, the skin portions move toward each other and into engagement and assume an undulating configuration at the interface therebetween. The apparatus further comprises a cartridge positioned adjacent the jaws and adapted to support a plurality of elongated skin attaching members.

Each skin attaching member is preferably a rod-like member having a sharp pointed tip at the distal end to facilitate subcuticular penetration of the skin. In one embodiment, each rod-like member is circular in cross section and may include at least one slot extending at least partially around a peripheral portion thereof. In another embodiment, the rod-like members are substantially rectangular in cross section. Indentations may also be formed in the rods to improve retention in the tissue. This facilitates manufacture of the rods, improves feeding of the rods and increases their retention characteristics.

In the preferred embodiment the cartridge is adapted to contain a plurality of the rod-like members and includes means to resiliently bias the rod-like members toward a position for advancing the member distally toward the body tissue when the body tissue is gripped by the sharp pointed members. The members are of length sufficient to engage oppositely sloped skin portions as determined by the dimensions and relative spacing of the pointed tips. Further, the rod-like members may include means on the outer surface to retain them in position within the body tissue.

A method is also disclosed for attaching two adjacent end portions of skin surrounding an opening comprising gripping one marginal end portion of the skin adjacent the opening at two spaced locations, gripping the opposite marginal end portion of the skin at a location generally medial of the two locations at which the first marginal end portion is gripped, displacing the two end portions of skin surrounding the opening toward each other sufficient to cause the end portions to engage each other and to assume an undulating shape, and introducing an elongated staple into the end portions of the skin subcuticularly, the elongated staple being of length sufficient to penetrate at least two spaced portions of skin on the same side of the opening so as to retain the marginal end portions together in end to end contacting relation to promote healing. As noted, the method may comprise configuring the staple to have an irregular outer surface to prevent the staple from working itself out of the subcuticular region. Various configurations of the staple are also contemplated.

Preferably, the method is practiced utilizing sharp skin engaging members attached to jaws as described to permit gripping the skin and bringing the end portions adjacent an opening to form the undulating shape.

According to the method contemplated, the staple may also be inserted subcuticularly.

BRIEF DESCRIPTION OF THE ACCOMPANYING FIGURES

Preferred embodiments of the invention are described hereinbelow with reference to the drawings herein:

FIG. 9 is a greatly enlarged view of an alternate embodiment of the staple of the present invention;

FIG. 10 is a greatly enlarged view of another alternate embodiment of another staple of the present invention;

FIG. 11 is a cross-sectional view of the staple of FIGS. 9 and 10; and

FIG. 12 is a cross-sectional view of several staples shown in stacked relationship.

DETAILED DESCRIPTION OF THE PREFERRED EMBODIMENTS

Figure 1:
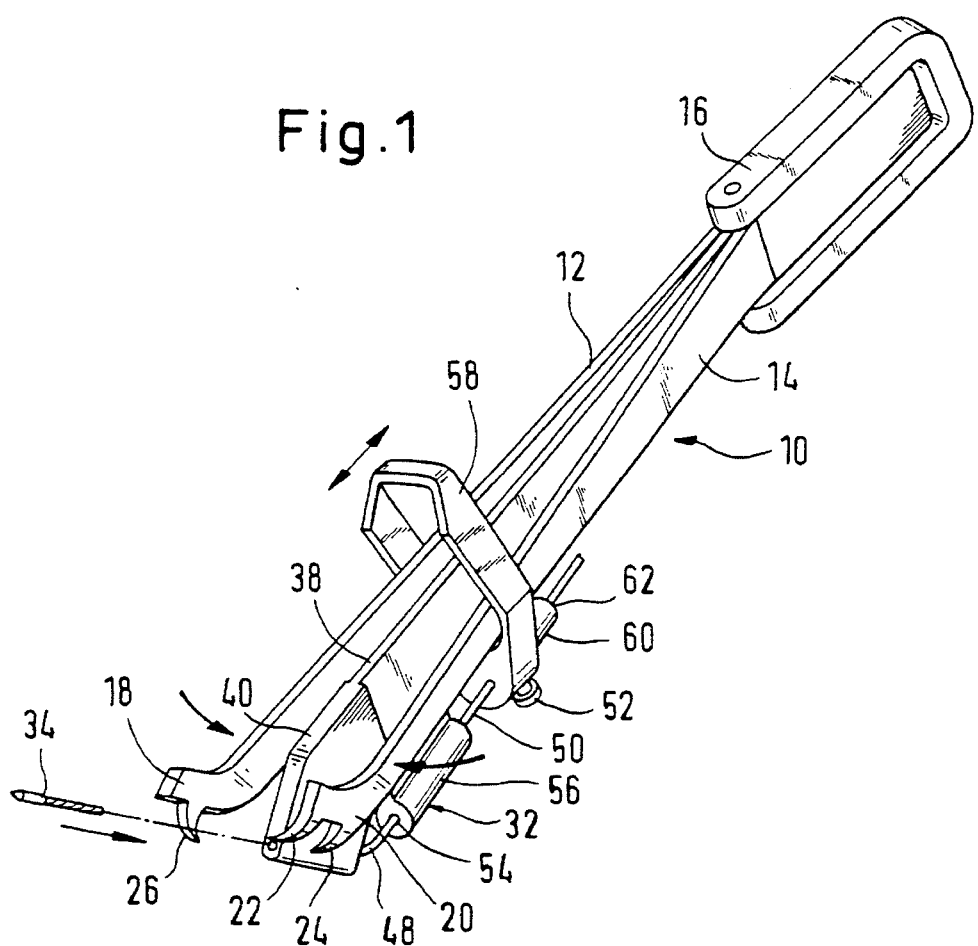
FIG. 1 is a perspective view of the apparatus for stapling body tissue according to the invention.

FIG. 1 illustrates the apparatus 10 for subcuticular stapling of skin, constructed according to the present invention. The apparatus 10 includes elongated arms 12 and 14 connected as shown by end bracket 16 and resiliently biased away from each other. The resilient outward bias may be provided naturally by fabricating the arms 12 and 14 of a resilient material such as spring steel, or optionally may be provided by incorporating a separate resilient spring in region of connecting bracket 16.

The lower end portion of each arm is constructed as shown. Arm 12 includes an extension or jaw 18 oriented at an appropriate obtuse angle with respect to the main portion of the arm and arm 14 includes a similar extension or jaw 20 as shown. The extension 20 includes sharp pointed skin gripping tips 22, 24 spaced apart from each other and extending generally downwardly and toward extension 18. Extension 18 includes a similarly shaped skin gripping tip 26 oriented generally downwardly and extending toward extension 20. The position of skin gripping tip 26 on extension 18 is preferably such as to be located medially between skin gripping tips 22, 24 when the arms 12 and 14 are manually brought together to grip the skin surrounding an opening as will be described. Each skin gripping tip 26, 22, 24 includes a broad base area to facilitate grasping the skin with minimum cutting after the sharp tip has penetrated the surface. Alternatively, a different number of skin gripping tips could be provided on each arm.

Figure 2:
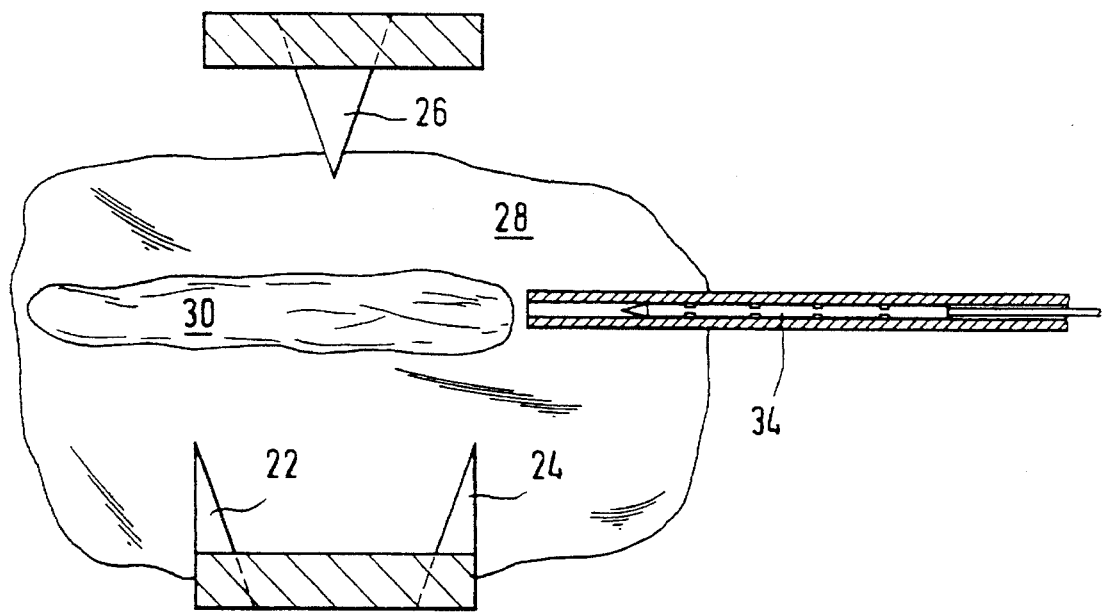
FIG. 2 is a view from above, greatly enlarged, illustrating the pointed gripping members of the apparatus of FIG. 1 prior to gripping the body tissue for subcuticular attachment.
Figure 3:
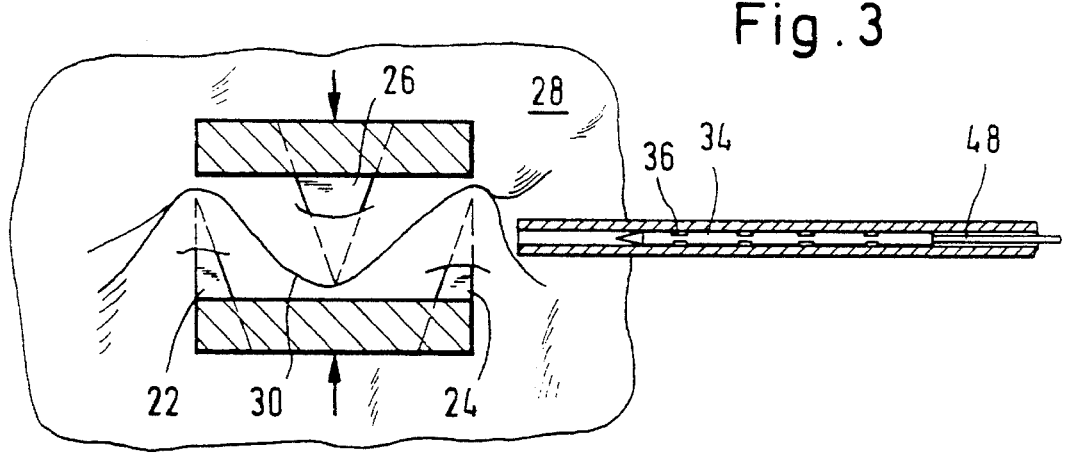
FIG. 3 is a view from above, greatly enlarged and partially in cross-section, of the pointed gripping members of the apparatus of FIG. 1, just prior to subcuticular introduction of a staple.
Figure 4:
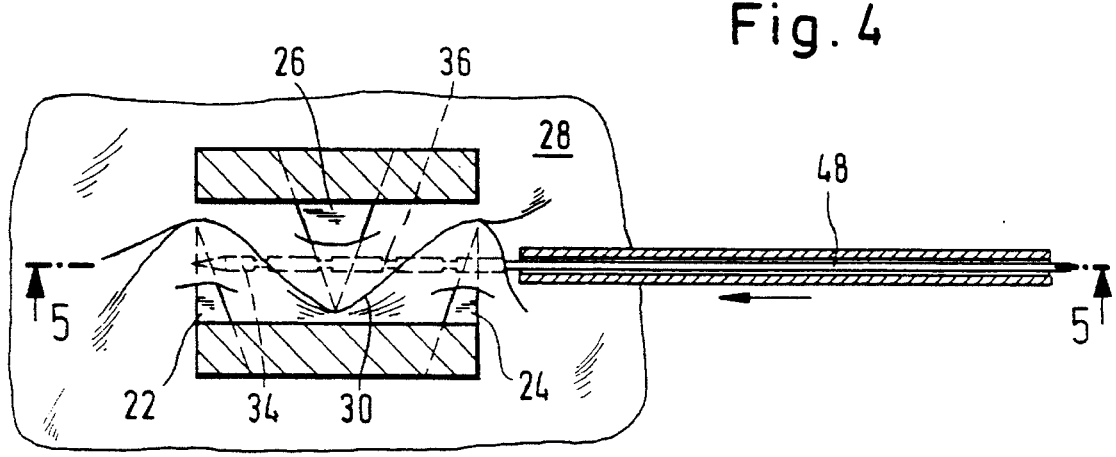
FIG. 4 is a view from above, similar to FIG. 3 after subcuticular introduction of the staple.

Referring now to FIG. 2, the basic operative principles of the invention will be described. There is illustrated the upper surface of skin 28 surrounding an opening such as a wound or surgically provided opening. The apparatus is positioned such that extensions 18, 20 may be positioned in contact with, and generally parallel to the upper surface of the skin. To close the opening in the skin the extensions are advanced downwardly against the skin sufficient to cause piercing tips 22, 24 and 26 to pierce the skin minimally as shown. Thereafter, the arms 12, 14 are squeezed together by the surgeon to cause the three sharp tips to join the skin portions surrounding the opening as shown in FIG. 3, i.e. to assume an undulating, or sinusoidal shape. Then, the staple actuating mechanism 32 is fired to cause the elongated staple 34 to penetrate the tissue below the upper epidermal layer and to retain the separate portions of skin in interfacial engaged relation as shown in FIG. 4. Thus, the opening in the skin is prepared for natural permanent healing and adhesion with minimum or no scarring.

Figure 5:
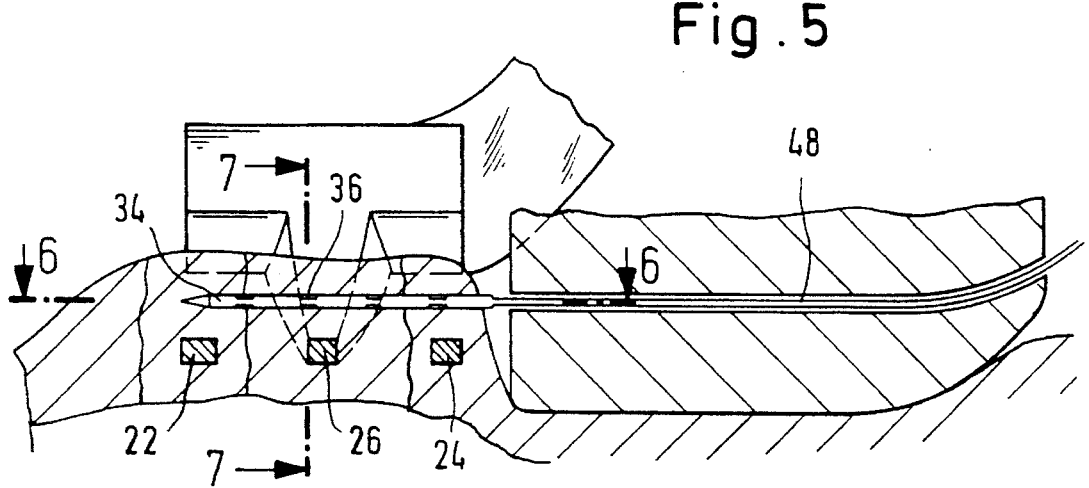
FIG. 5 is a view partially in cross-section, taken along lines 5—5 of FIG. 4 and illustrating one embodiment of the subcuticularly positioned staple after firing the apparatus.

Referring to FIG. 5 there is illustrated a cross-sectional view taken along lines 5—5 of FIG. 4, showing the sharp tips 26, 22 and 24 in position securing the skin surrounding the opening 30 with staple 34 fired in position. At this point in the closing sequence, the inward pressure on arms 12, 14 of the apparatus may be relieved to permit them to be opened by the resilient spring action and the sharp tips may be removed from the skin. Depending upon the nature and size of the opening in the skin, one or more of the staples may be fired in sequence and in adjacent end to end relation sufficient to maintain the opening in closed condition to promote healing. Thus, the nature of the staple and the capability of repeated firing will now be described.

The staple according to the invention is preferably constructed as a sharp tipped elongated member of naturally bioabsorbable material such as synthetic polymers or copolymers possessing a significant number of short-chain polyester linkages or other readily hydrolyzable linkages in their structure as, for example, is the case with polyglycolic acid, lactide-glycolide polymers, polydioxanone, polyalkylene glycols, polytrimethylene carbonate, polycaprolactone, their copolymers and related materials. One preferred material is made of a copolymer of lactide and glycolide made from approximately 90% m glycolide and approximately 10% m lactide. Another bioabsorbable material is made of a copolymer of lactide and glycolide made from approximately 25% m glycolide and approximately 75% m lactide blended with a homopolymer of polyglycolide so that the total composition is composed of approximately 42% glycolide. Other bioabsorbable materials for constructing the staple are disclosed in U.S. Pat. No. 4,523,591 to Kaplan et al. and U.S. Pat. No. 4,744,365 to Kaplan et al., herein incorporated by reference.

Figure 6:
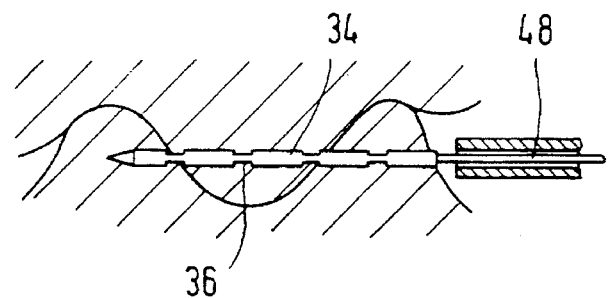
FIG. 6 is a view partially in cross-section, taken along lines 6—6 of FIG. 5.
Figure 7:
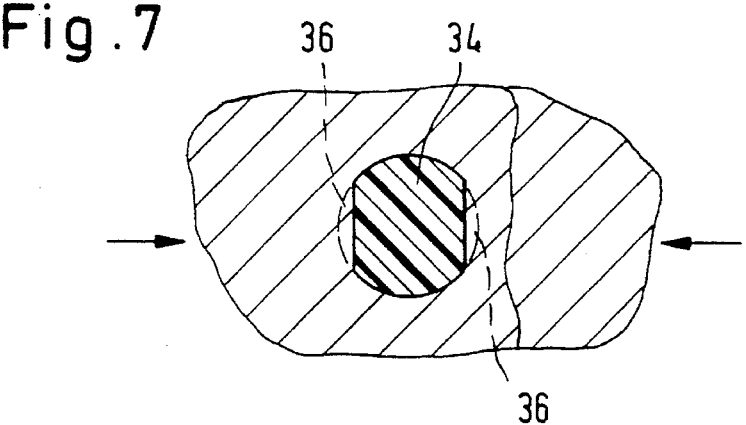
FIG. 7 is a cross-sectional view, greatly enlarged, taken along lines 7—7 of FIG. 5, illustrating one embodiment of the staple subcuticularly embedded in the skin portions attached thereby.

In the embodiment of a staple or fastening member shown in FIGS. 5 and 6, the fastening member is in the form of a rod or pin having a generally circular cross-section and must be of length at least sufficient to extend over at least two oppositely sloped surfaces of the skin on one side of the opening in order to prevent the staple from readily working its way out of the skin. To promote an even greater capability to maintain the portion of the staple in the skin, the staple preferably includes up to five or more slots 36 spaced along the length thereof to provide an irregular surface in engagement with the skin. This provides further stability to the staple and assists in preventing the staple from working its way out of the skin while retaining its rod-like configuration after application. The slots 36 may extend partially around the staple as shown in cross-section in FIG. 7, or they may be annular as to extend completely around the staple. It will be seen that in the preferred embodiment shown in the cross-section of FIG. 7, the slots 36 extend approximately between the 2 o'clock and 5 o'clock positions and the 7 o'clock and 10 o'clock positions. This feature is particularly significant in view of the undulating shape which the skin assumes at the interface between the two faces of the opening 30, which provides an environment for the rod to otherwise work itself out of the skin when the skin portions are shifted due to motions of the body.

The annular slots in the staple provide sufficient ridges and surface directional changes which engage the skin to prevent self working of the rod out of the skin. This feature is more clearly illustrated in FIG. 6 which shows the skin portions 28 surrounding the opening in cross-section and the staple 34 embedded therewithin. In one embodiment, the staple may be approximately 0.350 inch in length, have a major outer diameter between 0.015 and 0.016 inch and a minor dimension at the slots of between 0.012 and 0.013 inch. Preferably, the staple is of length at least equal to the dimension between the sharp skin engaging tips 22, 24 on extension 20. Clearly, however, the dimensions may be varied, depending upon the particular application contemplated.

The circular shaped rod of FIGS. 5 and 6 is one example of the staple (fastening member) of the present invention which can be utilized to fasten the undulating skin. In an alternate embodiment shown in FIG. 9, the staple 70 is in the form of a rod or pin which is generally rectangular in cross section. In the illustrated embodiment, it is substantially square in cross section. Rod 70 is elongated and of sufficient length to extend over at least two oppositely sloped surfaces of the skin on one side of the opening. The tapered tip 72 at the distal end of rod 70 has a sharp point 74 to facilitate penetration through the skin. In an alternate embodiment shown in FIG. 10, rod 80 is also of substantially square cross section, and has a tapered tip 82 with a sharp point 84. The rod 80 includes an indentation 86 adjacent its distal end and an indentation 88 adjacent its proximal end to improve the retention of the rod by restricting proximal and distal movement. That is, since the tissue stretches during penetration of the rod and then retracts, the edge of the indentation will restrict movement. Although only one indentation is shown at each end, clearly additional indentations can be formed along the length to improve retention. The indentations can be formed on opposing surfaces or the indentations can extend along all side surfaces. Proximal end surface 87 of rod 80 and proximal end surface 77 of rod 70 are adapted to be contacted directly by a pusher for driving the rod which will be described below. The rod is sufficiently rigid to substantially retain its elongated shape upon insertion. The rectangular shaped configuration of the rods facilitates stacking of the rods within staple cartridge 40 as described below. This configuration also provides for improved retention within the skin as the rods do not work their way out of the skin as easily as the rounded shaped rods.

The rods of FIGS. 9 and 10 also have the advantage in accommodating inaccuracies in molding techniques. Line P represents the parting line of the two half molds utilized in forming rods 70 or 80. The accuracy of molding the rods of FIGS. 9 and 10 can be improved by forming the rod with cut edges 90 so that the parting line P for the half molds is located at a non-critical point i.e. along edges 90. That is, the more critical dimensions (e.g. length) of edges 92, 94, 96 and 98 can be maintained substantially constant even if the edges 90 are not aligned as a result of joining the two half molds during formation of the rod. In other words, any variation in the widthwise dimension as a result of misalignment during formation will not significantly vary the length of the more critical edges.

Cut or flattened edges 90 also provide a smoother surface for the rods 70, 80, thereby preventing cutting of the tissue which might otherwise occur if the junction of edges 92, 94, 96, 98 was a single point as in a perfect square.

Clearly, other shapes of rods are within the scope of the present invention as long as they are sufficiently elongated to penetrate at least one of the undulating portions of the opposing skin areas. For example, rods of hexagonal cross section could be provided.

The dimensions of the rod can vary depending on its use. By way of example only, in one embodiment the length of the rod 70 can range from 0.440 to 0.445 inches, the length of each side edge (e.g. edges 92, 94, 46 and 98) can range from approximately 0.0245 to 0.0265 inches and the length of edge 90 can range from approximately 0.0036 to 0.0056 inches. In this embodiment, the tapered tip forms a point at an approximate 30° angle and the tip portion can have a length ranging from approximately 0.0653 to 0.0693 inches. If an indentation is provided, the indentation can have a depth of approximately 0.003 to 0.004 inches. Clearly, these dimensions are provided solely by way of example as rods of other dimensions are also within the scope of the present invention.

Figure 8:
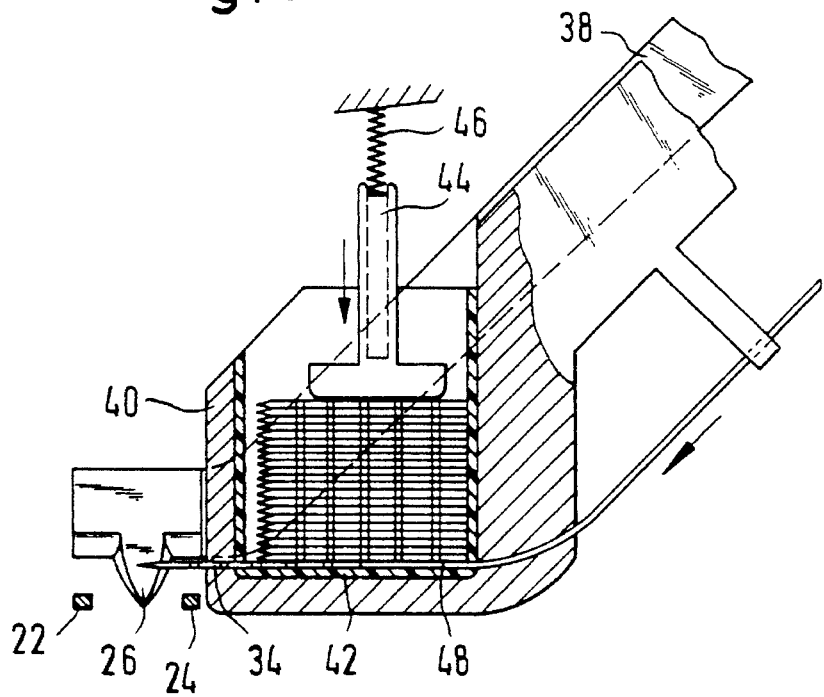
FIG. 8 is a greatly enlarged side view, partially in cross-section, illustrating the staple cartridge which forms part of the invention.

Referring to FIG. 8 in conjunction with FIG. 1, one embodiment of a staple cartridge is illustrated which can provide repeated firing of staples subcuticularly into the skin as shown in FIG. 1. The apparatus includes a central arm 38 with staple cartridge 40 attached to the lower end. The cartridge contains a plurality of staples 34 in vertically stacked relation as shown in FIG. 8, biased downwardly toward the firing chamber 42 by a plunger 44 and resilient spring arrangement 46 shown schematically in FIG. 8. Thus after each staple is fired, the staple next in line automatically positions itself in the chamber 42 under downward action of plunger 44. The cross-sectional dimension of chamber 42 is equal to or slightly greater than the major diameter of the staple 34 to facilitate a snug fit for the staple in the chamber. The length of cartridge 40 and chamber 42 is at least equal to the length of the staples.

The configuration of rods 70 and 80 facilitates stacking as they can be stacked along their straight edges. Rods 70 can be vertically stacked in a similar fashion as rods 34. Alternately, as shown in FIG. 12, rods 70 can be diagonally stacked along edge 94. This advantageously conserves space as compared to the vertical stacking of rods 34. Rods 80 can be stacked in a similar fashion as rods 70. Clearly, the cartridge would be appropriately configured to accommodate the diagonally stacked rods.

The firing mechanism includes a staple firing plunger in the form of a flexible plunger wire 48 which is slidable through staple firing chamber 42 to engage the staple next in line to cause it to advance into the skin at a subcuticular level. The cross-section of firing wire 48 approximately matches the cross-section of staple 34 or of staple 70 and is attached at the proximal end to rod 50 as shown in FIG. 1, which is slidable within opening 54 in guide housing 56 such that proximal upward movement of rod 50 causes withdrawal of wire 48, and distal downward movement thereof causes firing action by wire 48 on staple 34. Staple firing may be accomplished by manual downward distal movement of ring 58 attached to rod 50 as shown by set screw 52. Withdrawal of firing wire 48 out of firing chamber 42 is accomplished by manually moving ring 58 (and rod 52) proximally upwardly to permit the next staple 34 to enter the firing chamber 42 under downward action of spring 46. Further guidance for rod 50 is provided by proximally located second external guide housing 60 which contains a second guide opening 62 for reception of rod 50. Thus the two guide housings 56 and 60 serve to firmly position rod 50.

The firing movements of wire 48 may be adjusted by resetting the position of rod 50 relative to ring 58 by loosening set screw 52 and setting the desired position of rod 50. Further, it is noted that guide openings 54 and 62 are circular in cross-section almost equal to or slightly greater in dimension than rod 50. Sufficient clearance is provided to guide rod 50 yet to maintain steady slidable movement of the rod. Plunger wire 48 has a cross-sectional dimension slightly less than staple firing chamber 42 but sufficient to maintain steady distal and proximal movement therewithin while engaging the proximal end face of the staple. The staple 34 and the firing wire 48 are similarly dimensioned in cross-section, at least at the proximal end, such that engagement of the proximal surface of the staple by the wire 48 results in even and steady distal movement of the staple when the wire is advanced distally.

In operation, the apparatus is inserted into the opening in the skin closest to one end with the jaws 18, 20 positioned in respective engagement with the opposed marginal skin portions adjacent the opening. The jaws are advanced toward the skin sufficient to cause the sharp tips 26, 22 and 24 to grip the skin by piercing the outer layer or layers. Thereafter, the arms 12, 14 are manually drawn together to cause the skin to engage each other and to form an irregular, or undulating shape. At this time, the staple 34 is fired into the cutaneous matter as shown in FIG. 4 to retain the opposed skin portions together. The jaws are then withdrawn from the skin and the procedure is repeated in the area next adjacent the inserted fastener a sufficient number of times to close the entire opening in the skin.

Although a preferred embodiment of the multiple fire staple cartridge has been described, the structures and embodiments of alternative staple magazines may be utilized in combination with the multiple tip attachment feature which permit subcuticular stapling of an opening in body tissue. Further, although the preferred embodiment herein contemplates subcuticular attachment of cutaneous matter, it is well within the contemplated invention to apply such staples at subcutaneous levels, ie. below the epidermis and dermis. Such applications would involve minor variations of the dimensional relation between the sharp tips 22, 24 and 26 and the staple firing chamber 42.

It can be readily appreciated that a surgical opening or wound in the skin can be stapled utilizing the apparatus of the invention, leaving little or no extraneous staple markings or puncture wounds. Further, the resulting opening in the skin can be attached with greater precision and accuracy with the result that improved healing may be promoted with less visible wound indicia.

What is claimed is:

1. A surgical apparatus for attaching two portions of body tissue, which comprises:

a pair of opposed jaws each having a member to engage one portion of the body tissue, means supporting said jaws for moving at least one of said jaws toward the other jaw to move said body tissue portions toward one another;

a chamber supported proximally of said jaws for holding a plurality of rod-like members; and a plurality of rod-like members disposed in said chamber, each rod-like member being elongated and of sufficient length to penetrate said body tissue portions when drawn together, each rod-like member further being substantially rectangular in cross-section.

2. A surgical apparatus as recited in claim 1, wherein each said rod-like member comprises a distal end having a tapered tip having a sharp point for penetrating the body tissue and a proximal end.

3. A surgical apparatus as recited in claim 2, wherein said chamber is dimensioned to receive and support said rod-like members in diagonally stacked relation.

4. A surgical apparatus as recited in claim 3, further comprising means for driving said rod-like members outwardly from said chamber into the body tissue.

5. A surgical apparatus as recited in claim 2, further comprising an indentation formed adjacent said proximal end of each said rod-like member to restrict linear movement after insertion into the body tissue.

6. A surgical apparatus as recited in claim 2, wherein said rod-like members are composed of a bioabsorbable material.

7. A surgical apparatus for attaching at least two portions of body tissue, which comprises:

a) a pair of jaws respectively supported in opposed relation, each jaw having a member to engage one portion of the body tissue, at least one of said jaws movable toward the other jaw to move the body tissue portions toward one another;

b) a chamber for supporting a plurality of rod-like members, said chamber disposed and supported proximally of said jaws, each said rod-like member being of sufficient length to penetrate the two body tissue portions when drawn together, each said rod-like member having a cross-sectional configuration to facilitate stacking of said rod-like members in contacting relationship; and c) a pusher movable within said chamber for advancing said rod-like members into the at least two body tissue portions without substantial deformation thereof.

8. A surgical apparatus as recited in claim 7, wherein each said jaw is respectively supported so as to be movable toward and away from the opposed jaw to move said body tissue portions toward one another to a position wherein said body tissue portions are drawn together in close approximation, and wherein each said rod-like member is individually movable to penetrate said body tissue portions when drawn together in close approximation.

9. A surgical apparatus as recited in claim 8, wherein each said rod-like member has at least one substantially planar surface which extends longitudinally along said rod-like member, whereby said rod-like members are laterally stacked along said longitudinally extending planar surfaces to form a stacked arrangement.

10. A surgical apparatus as recited in claim 7, wherein said rod-like members are stacked laterally in surface-to-surface contact.

11. A surgical apparatus as recited in claim 7, wherein said cross-sectional configuration of each said rod-like members is square.

12. A surgical apparatus as recited in claim 7, wherein said cross-sectional configuration of each said rod-like members is hexagonal.

13. A surgical apparatus as recited in claim 7, wherein said rod-like member is of substantially circular cross-section.

14. A surgical apparatus for attaching two portions of body tissue, which comprises:

a pair of opposed jaws, each jaw having a member adapted to engage one portion of the body tissue, at least one of said jaws movable towards the other jaw to move the body tissue portions toward one another; and a plurality of rod-like members disposed and supported proximally of said jaws, each said rod-like member being of sufficient length to penetrate the two body tissue portions when drawn together, each said rod-like member having a rectangular cross-sectional configuration to facilitate stacking of said rod-like members; and a pusher engageable with said rod-like members for advancing said rod-like members into the body tissue portions.

15. A surgical apparatus as recited in claim 14, wherein each rod-like member includes at least three planar outer surfaces extending longitudinally therealong.

16. A surgical apparatus as recited in claim 14, wherein each rod-like member is of sufficient rigidity to substantially retain said substantially straight elongated shape upon insertion into body tissue.

17. A surgical apparatus for attaching two portions of cutaneous body tissue, which comprises:

a pair of opposed jaws, each jaw having a member to engage one portion of the body tissue, at least one of said jaws movable toward the other jaw to move the body tissue portions toward one another; and a plurality of rod-like members disposed and supported proximally of said jaws, each said rod-like member being of sufficient length to penetrate the two body tissue portions when drawn together, each said rod-like member having a side portion adapted to cooperate with a side portion of an adjacent rod-like member to facilitate lateral stacking of said rod-like members; and a pusher engageable with said rod-like members for advancing said rod-like members into the body tissue portions.

18. A surgical apparatus as recited in claim 17, further comprising an indentation formed in said distal end of said rod-like member to restrict linear movement of said rod-like member after insertion into the body tissue.

19. A surgical apparatus as recited in claim 17, wherein said rod-like members have a substantially straight elongated shape and are of sufficient rigidity to substantially retain said substantially straight elongated shape upon insertion into body tissue, said rod-like members each defining a longitudinal axis extending therethrough, and applied to the body tissue in general alignment with said longitudinal axis.

* * * * *